United States Patent [19]
Jerrold-Jones et al.

[11] 4,012,308
[45] Mar. 15, 1977

[54] ION SENSITIVE COMBINATION ELECTRODE

[75] Inventors: Paul Jerrold-Jones, Claremont; Irwin H. Krull, Santa Ana, both of Calif.

[73] Assignee: Beckman Instruments, Inc., Fullerton, Calif.

[22] Filed: Nov. 7, 1975

[21] Appl. No.: 629,833

[52] U.S. Cl. .......................... 204/195 F; 128/2 E; 204/195 G
[51] Int. Cl.$^2$ ................ G01N 27/30; G01N 27/36
[58] Field of Search .......... 204/1 H, 195 G, 195 F, 204/195 R; 324/30 R, 29; 128/2 E, 2.1 E

[56] References Cited

UNITED STATES PATENTS

| | | | |
|---|---|---|---|
| 3,188,285 | 6/1965 | Watanabe | 204/195 G |
| 3,551,315 | 12/1970 | Friconneau et al. | 204/195 G |
| 3,677,925 | 7/1972 | Tamate et al. | 204/195 R |

FOREIGN PATENTS OR APPLICATIONS

| | | | |
|---|---|---|---|
| 729,575 | 5/1955 | United Kingdom | 204/195 F |

*Primary Examiner*—G. L. Kaplan
*Attorney, Agent, or Firm*—R. J. Steinmeyer; R. R. Meads; J. R. Shewmaker

[57] ABSTRACT

An electrochemical combination electrode assembly particularly adapted for measuring the pH of body portions of a living subject, such as skin, hair, and the like, and which can be operated in any vertical, inclined or horizontal orientation. The assembly comprises a pH-indicating glass electrode supported within a tubular plastic container and includes a generally flat, pH-sensitive structure at a sensing end of the assembly. Conventional indicating and reference half-cell electrodes are supported in separate reservoirs of the assembly containing internal and reference electrolytes, respectively. The upper ends of the reservoirs are sealed by elastomeric plugs which compensate for differing coefficients of expansion within the assembly and coact with the electrolytes to prevent formation and migration of air bubbles to the sensing end of the assembly. In addition, a capillary passage is situated between the top of the internal electrolyte and the seal therefor to accommodate expansion of the internal electrolyte. A liquid junction structure, comprising a plurality of capillary paths, is spaced around the pH-sensitive structure and connects the reference electrolyte with the sample to be measured. A conductive cap, disposed over an end opposite the sensing end of the assembly and electrically connected to the reference half cell, shields the assembly from outside electrical interference and additionally provides a handle for hand manipulation of the assembly.

11 Claims, 3 Drawing Figures

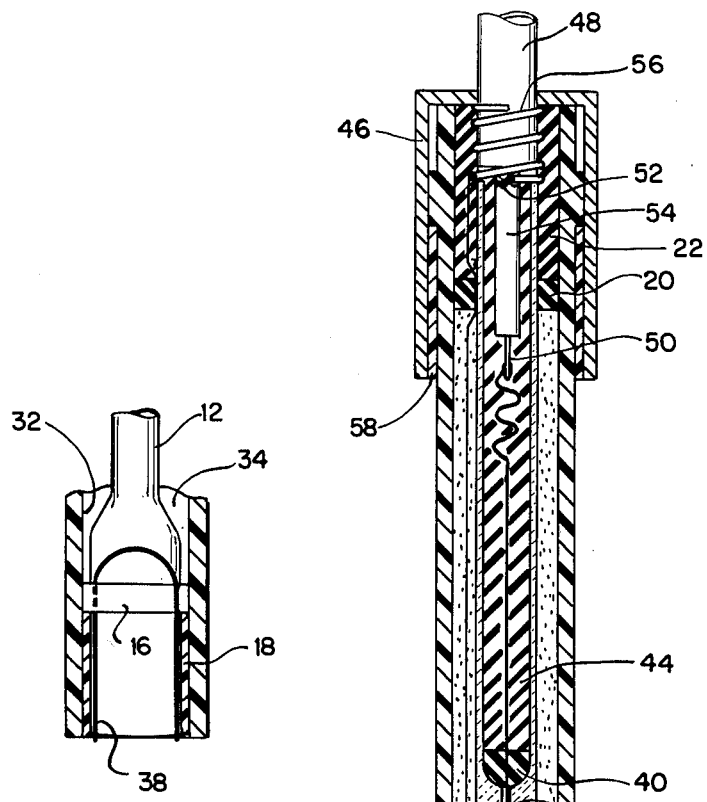
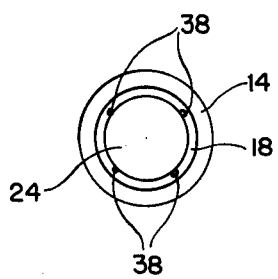
FIG. 3
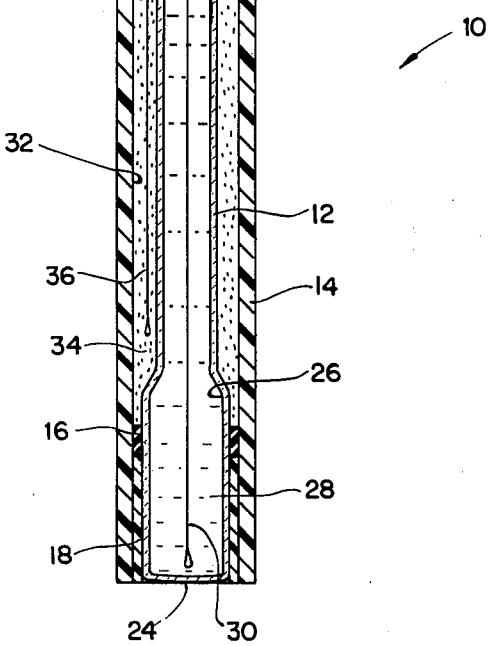
FIG. 2
FIG. 1

ION SENSITIVE COMBINATION ELECTRODE

BACKGROUND OF THE INVENTION

1. Field of the Invention

The present invention relates to electrochemical electrodes and, more particularly, to combination electrodes for measuring the ion concentration of solutions.

2. Description of the Prior Art

Combination electrodes comprising a sensing portion and a reference portion incorporated in a glass or a plastic structure are known in the art. One known electrode assembly for measuring pH includes a generally flat, pH-sensitive glass membrane having one face for contacting a sample to be measured and an opposite face contacting an internal electrolyte within the assembly. In addition, a liquid junction is provided between the sample and a reference electrolyte within the assembly. By virtue of its flat ion-sensing structure the electrode assembly is able to measure a small quantity of sample solution on a relatively flat surface without the need to immerse the electrode in a large volume of the solution. Thus, the electrode is particularly suited for measuring, for example, the pH of moisture on the skin of a human subject.

While electrodes of the foregoing nature have performed satisfactorily, they have been confined generally to laboratory, clinical, or other specialized applications requiring trained operating personnel. Further, the sensing portion of such prior electrode assemblies must be carefully positioned on the sample to be measured with the electrode assembly vertically oriented with respect to the sample. This is necessary to ensure that the conventional liquid junction included in the prior art electrode makes contact with the sample and to ensure that any air bubbles within the electrode assembly rise to the top thereof so as not to contact either the ion-sensitive membrane or the liquid junction. If these precautions are not taken, erroneous measurements can result. In addition, the reference electrolyte is generally consumed during normal operation of the electrode and must be periodically refilled. The refilling operation requires a skilled operator to ensure that a proper electrolyte is employed and that no contamination is introduced during the filling operation.

Recently, the need has arisen for a combination electrode assembly which can be operated over prolonged time periods at any physical orientation by non-technical operators. For example, a particular need exists in the cosmetic and hairdressing industry for an electrode assembly which can be routinely employed by hairdressers, beauty operators, and the like for monitoring the pH of a subject's hair, skin, or other body parts. The present invention provides such an assembly.

SUMMARY OF THE INVENTION

Briefly and in general terms, the present invention resides in a new and improved ion-sensitive combination electrode assembly of commercially practical form which overcomes the disadvantages of the prior electrodes. The electrode assembly is simple, rugged, and inexpensive in construction and is easily operated in any physical orientation. Moreover, the electrode assembly exhibits minimal electrolyte leakage, is reasonably small in size, is electrically shielded and insulated from outside electrical interference, and is highly reliable in operation.

To these ends, and in accordance with a primary aspect of the invention, reference and internal electrolyte reservoirs within the electrode assembly are sealed by means for preventing formation and migration of air bubbles in the electrolytes regardless of the physical orientation of the assembly. Preferably this is accomplished by sealing each electrolyte reservoir with an elastomeric sealing disc or plug which is expandable to compensate for different temperature expansion characteristics within the assembly. In particular, in a preferred form of the invention, an elastomeric seal for the reference electrolyte reservoir directly contacts the reference electrolyte while a separate elastomeric seal closes an exposed end of a small capillary passage located at an upper end of the internal electrolyte reservoir leaving a small compressible air volume within the passage and above the internal electrolyte into which the electrolyte can expand.

Secondly, the electrode assembly of the present invention includes an ion-sensitive structure at one end and a liquid junction structure comprising a plurality of capillary paths spaced around the ion-sensitive structure and communicating with the reference electrolyte within the assembly to ensure adequate contact between the sample solution and at least one capillary path in any orientation of the electrode assembly.

Further, a conductive cap over an end opposite the sensing end of the electrode assembly serves as a handle for hand manipulation of the assembly and is, in addition, electrically connected to the reference portion thereof to shield the assembly from outside electrical interference.

Other advantages of the invention will be apparent from the following description taken in conjunction with the accompanying drawings.

BRIEF DESCRIPTION OF THE DRAWING

FIG. 1 is a cross-sectional view, in a generally vertical plane, through a combination electrode assembly of the present invention.

FIG. 2 is a bottom plan view of the assembly of FIG. 1.

FIG. 3 is a fragmentary view of the sensing end of the assembly of FIG. 1 partially cut away to illustrate the positioning of the asbestos fiber liquid junction structure therein.

DESCRIPTION OF THE PREFERRED EMBODIMENT

As shown in the drawing for purposes of illustration, the invention is embodied in an ion-sensitive, combination electrode assembly, indicated generally by numeral 10. The electrode assembly 10 comprises an indicating electrode 12 supported near its opposite ends to extend coaxially within a generally tubular container 14 formed of a durable nonconductive material such as polyethylene, polypropylene, or a fluorocarbon plastic. As illustrated in FIG. 1, the support for a lower end of electrode 12 within the container 14 preferably comprises a sleeve-like structure disposed in a void between the lower ends of the electrode and the container and includes an elastomeric band or plug 16 and an adhesive layer 18, both of silicone rubber. Plug 16 is situated vertically above the adhesive layer 18 and limits the upward flow of the adhesive 18 into the void. Similarly, the support for an upper end of the electrode comprises an elastomeric sleeve-like structure of silicone rubber including an annular sealing band or plug 20 and an adhesive layer 22 disposed in an annular space between the upper ends of the electrode and the container.

For measuring pH, the indicating electrode 12 comprises a generally tubular, glass electrode body having a slightly enlarged lower or sensing end closed by a membrane 24 of pH-sensitive glass. The interior of the indicating electrode 12 defines a first or internal electrolyte reservoir 26 immediately adjacent membrane 24 and filled with a suitable electrolyte 28, such as an aqueous solution of potassium chloride. A conventional indicating half cell 30 comprising a silver wire conductor coated at its lower end with silver chloride extends axially into the internal reservoir and is immersed in the electrolyte 28.

While the interior of the electrode 12 adjacent the membrane 24 defines the internal reservoir 26, the annular space above the plug 16 and between the exterior of the electrode and the interior of the container 14 defines a second or reference electrolyte 32 filled with a suitable electrolyte 34, such as potassium chloride. In the preferred embodiment, electrolyte 34 is a gel instead of solution to minimize electrolyte loss during operation of the assembly. A conventional reference half cell 36 comprising a silver wire conductor coated at its lower end with silver chloride extends axially into the reference electrolyte reservoir and is immersed in the electrolyte 34.

As illustrated, the pH-sensitive membrane 24 of the indicating electrode 12 has a generally flat exterior surface substantially coplanar wth the lower end of the container 14 and adapted to contact sample solutions the pH of which is to be measured. Thus, the electrode assembly 10 presents a substantially flat sensing surface to a sample and, as a result, is ideally suited to measure the pH of small quantities of solutions such as those found on the scalp, skin, or other body parts. Of course, measurements with electrode assembly 10 are not confined to flat surfaces, and the assembly could be immersed in large solution volumes if desired.

In order that such pH measurements may be made, it is of course recognized that ionic communication must be made between the sample solution and the reference electrolyte within the reservoir 32. Further, in accordance with the present invention, such communication must be maintained irrespective of the physical orientation of the assembly relative to the sample, be it vertical, inclined or horizontal. To provide such communication in the assembly 10, a liquid junction or leak structure is formed at the sensing end of the assembly surrounding the pH-sensitive membrane 24. As illustrated in FIGS. 2 and 3, the liquid junction structure comprises several strands 38 of asbestos, linen, or other suitable capillary material extending from the flat sensing surface of the assembly through the length of adhesive layer 18 and through band 16 into the reservoir 32 containing the reference electrolyte 34.

As illustrated in FIG. 2, the capillary material 38 is exposed at the sensing surface of the assembly at four locations equally spaced around the circumference of the indicating electrode 12. This structure may be provided by inserting two looped strands of asbestos fiber between band 16 and the body of indicating electrode 12. FIG. 3 shows one such looped strand 38 with the two ends thereof terminating at the sensing face of the electrode assembly and the loop extending into contact with the reference electrolyte 34. While two looped fiber strands have been utilized in the preferred embodiment, it should be understood that any number of strands could be employed. By spacing the fiber ends around the circumference of the ion-sensitive membrane 24, it is apparent that contact between the sample material and at least one fiber end is assured irrespective of the physical orientation of the electrode assembly, thereby enabling the electrode assembly to contact the sample in different physical orientations.

To further enhance the ability to take measurements with the electrode assembly 10 at any orientation, the internal and reference electrolyte reservoirs 26 and 32 are closed and sealed by means for preventing formation and migration of air bubbles in the electrolytes. To this end, and considering first the internal electrolyte 28, a sealing disc or plug 40 of elastomeric sealing material, such as silicone rubber, is positioned within the indicating electrode 12 directly above the internal electrolyte 28. To minimize the area of possible contact between the plug 40 and the electrolyte 28, and thereby minimize the potential volume of air which can be trapped therebetween, a narrow constriction is formed within the electrode 12 intermediate the ends thereof providing a capillary passage 42 opening into the electrolyte reservoir. Preferably the capillary passage has a diameter just large enough to receive a syringe needle from the upper end of the electrode assembly to inject the electrolyte 28 into electrolyte reservoir 26. In this regard, the electrolyte reservoir is filled at least to the bottom side of passage 42. Then, after the indicating half cell 30 is inserted through a minute central bore in the plug 40, the plug and half cell are positioned together within the electrode 12 and the plug is pushed flush against the top side of passage 42. Finally, a lower portion of the space above plug 40 is filled with silicone rubber 44 which is cured tio permanently secure the plug 40 and half cell 30 in place.

It should be noted that when the electrolyte 28 is introduced only to the bottom side of capillary passage 42, the passage provides a compressible air chamber or pocket into which electrolyte 28 may expand when the electrode assembly is subjected to temperature fluctuations. Under such circumstances, however, the passage 42 should be dimensioned to produce a liquid surface tension at and across its lower open end which is sufficiently high to preclude escape of air from the passage into the internal electrolyte reservoir 26 and replacement of the escaped air with the internal electrolyte 28, regardless of the physical orientation of the electrode assembly. While such surface tensions may be produced by passages of different dimensions for electrolytes of different viscosities, and while such dimensions may be determined by trial and error without the exercise of invention, suitable dimensions for the illustrated form of passage 42 have been found to be length, approximately 0.20 in., and passage diameter, approximately 0.04 in.

Of course, air in passage 42 can be eliminated by filling the passage with electrolyte 28 so that the elastomeric plug 40 is disposed in direct contact with the electrolyte. Also, the length of the passage can be reduced so that plug 40 is disposed adjacent the top of the electrolyte reservoir and the electrolyte 28 therein. In fact, if desired, the constriction and passage 42 can be eliminated entirely and plug 40 placed in direct contact with the internal electrolyte 28. In all of these modifications, however, the elastomeric silicone rubber plug alone must absorb any expansion of the electrolyte.

In accordance with a further aspect of the invention, the upper end of the reference electrolyte reservoir 32 is also closed and sealed by the elastomeric, annular sealing band or plug 20. As illustrated in FIG. 1, the plug 20 retains the conductor of reference half cell 36 against the body of indicating electrode 12 and directly contacts the upper surface of reference electrolyte 34 so that there is no air pocket therebetween. The remaining space above the annular plug 20 is filled with the silicone rubber 22 which is cured to permanently secure plug 20 in place.

In practice, it has been found that by preventing the formation of air pockets in the electrolyte reservoirs in the above manner, air bubbles do not migrate through the internal electrolyte 28 to the ion-sensitive membrane 24 or through the reference electrolyte 34 to the liquid junction structure 38 regardless of the physical orientation of the assembly. As a result, the electrode assembly can be employed in virtually any orientation, even upside down. Moreover, the silicone rubber plugs 40 and 20 prevent leakage of electrolyte from the electrolyte reservoirs and, in addition, provide expansive seals between the glass indicating electrode 12, the plastic container 14, and the electrolytes 28 and 34 thereby compensating for the different temperature coefficients of expansion of each. Additional temperature compensation is provided by the compressible air pocket within the capillary passage 42, which is dimensioned and sealed by plug 40 in a manner which prevents escape of air therefrom into internal electrolyte 28 and which thus prevents formation and migration of air bubbles in the internal electrolyte.

In addition to the prevention of air bubbles in the assembly, an important feature of the present invention is the combined electrical and handle forming characteristics of an electrically conductive, metal, cup-shaped cap 46 at an upper end of the assembly. As illustrated in FIG. 1, the cap 46 surrounds and shields the electrical connections of the half cell conductors 30 and 36 to a coaxial cable 48 which connects the electrode assembly 10 to a pH meter or the like. In this regard, the cable comprises a center conductor 50 disposed coaxially within and insulated from an internal shielding layer 52 of braided metal by a tubular insulating layer 54. A conductive metal spring 56 surrounds the cable and the bottom coil of the spring abuts the top rim of the indicating electrode 12. The reference half cell conductor 36 and the shielding layer 52 of the cable are both soldered to the metal spring 56 so that the spring electrically connects the reference half cell conductor to the shielding layer. The indicating half cell conductor 30 is soldered to the center conductor 50 of the cable. The cap 46 covers the upper end of the electrode assembly 10 and the foregoing connections and is held in place by an epoxy adhesive sleeve 58. The cap 46 includes a base portion through which the cable 48 passes from the assembly and a sidewall portion surrounding the upper end of tubular container 14. In this fashion, the cap sidewall provides a surface area for gripping the electrode assembly and manipulating it during use.

In order to provide electrical shielding for indicating half cell conductor 30, the sidewall of cap 46 extends downwardly along the tubular container 14 so that a portion of the sidewall circumscribes the reference electrolyte 34. Moreover, the cap 46 is electrically connected both to the reference half cell conductor 36 and to the shielding layer 52 of cable 48. In the preferred embodiment, such electrical connection to cap 46 is provided by the conductive spring 56 which is biased into electrically conductive, pressure contact with the interior surface of the base portion of the cap. As a result, cap 46 is at the potential of the reference half cell 36 and serves as an electrical shield surrounding the indicating half cell conductor 30 at the upper end of the electrode assembly. Reference electrolyte 34 in the annular reservoir 32 likewise surrounds and shields conductor 30 for most of the remainder of its length. As a result there is continuous shielding provided by the combination of the cap 46 and the reference electrolyte 34 for indicating half cell conductor 30 substantially throughout its length except at the extreme lower portion thereof. This eliminates the need for internal shielding layers conventionally employed in combination electrodes.

While the basic structure of the assembly 10 has been described hereinabove, an even clearer appreciation of the simplicity and novel features of the invention may be achieved from a consideration of the manner of assembly of the invention. In this regard, the internal electrolyte reservoir 26 of indicating electrode 12 is first filled with electrolyte 28 to capillary passage 42. The indicating half cell 30 is inserted through the passage into the electrolyte and the passage sealed by inserting plug 40 in place. The remaining volume above plug 40 is then partially filled with silicone rubber 44 and the silicone rubber cured to hold the plug in place. Band 16 is then slipped around the lower end of the electrode 12 with two loops of asbestos fiber strands 38 inserted between the band and the electrode. Thus assembled the electrode 12 is inserted into the tubular container 14, and the lower end of the electrode is secured to the container by silicone rubber adhesive 18 injected into the void between the container and the electrode.

Next the annular reference electrolyte reservoir 32 is filled with gel electrolyte 34 from the open (top) end of the assembly and reference half cell 36 inserted into the reservoir. Annular plug 20 is then inserted into the reservoir and pushed into contact with the gel electrolyte leaving no air space therebetween. A portion of the annular volume above plug 20 is then filled with silicone rubber 22 and the silicone rubber cured in order to secure the plug.

Finally, electrical connection is made to the electrode assembly 10. In this regard, the spring 56 and conductive cap 46 are slid onto coaxial cable 48 and the shielding layer 52 of the cable is wrapped around the lower coil of the spring and soldered thereto. Center conductor 50 of the cable is then soldered to indicating half cell 30, and the conductor and half cell are inserted into the indicating electrode body 12. Reference half cell conductor 36 is soldered to the lower coil of spring 56, and the remaining volume within indicating electrode 12 and the remaining annular volume between electrode 12 and container 14 are filled with silicone rubber 22 and 44 respectively to immobilize the cable 48, the spring 56, and all electrical connections thereto. Conductive cap 46 is then slid over the end of the electrode assembly in pressure engagement with spring 44 and secured in place by adhesive 58. As assembled, the electrode assembly is approximately 4⅝ in. in length and one-half inch in diameter.

From the foregoing it is evident that the electrode assembly 10 is extremely simple in design and operation and can be used routinely by non-technical operators without the normal precautions required for fragile combination electrode assemblies. Since plugs 40 and 20 seal the electrolytes in the assembly without formation and migration of air bubbles therethrough, the assembly can be operated in any physical orientation. The liquid junction structure surrounding the glass electrode 12 ensures sample contact at any orientation and thereby further facilitates operation on body surfaces, such as hair, skin or the like. The electrolytes are sealed in the assembly in a non-refillable manner eliminating refilling errors and reference electrolyte 34 is in gel form to minimize its loss during operation thereby increasing the operational life of the assembly. Conductive cap 46 provides both a convenient handle and an electrical shield for the assembly. With the rugged mechanical bonds and electrical connections between cable 48, half cell conductors 30 and 36, spring 56, and cap 46, the assembly can be repeatedly used without fear of mechanical damage or electrical breakdown. For example, in a beauty salon, the assembly may be hung for use near the subject to be measured and repeatedly removed and rehung in the course of shampooing without any special precautions to prevent erroneous readings or possible breakage of the assembly.

While the electrode assembly is illustrated for measuring pH, it should be understood that other ion-sensitive materials and structures could be employed for measuring ion activity other than pH. In applications where an indicating electrode assembly alone is desired which can operate at any orientation, an electrode assembly in the form of indicating electrode 12 (including elastomeric plug 40, capillary passage 42 and the aforementioned modifications thereof) can be employed in conjunction with a conventional individual reference electrode assembly. In this form, the upper end of the indicating electrode 12 would be closed by a suitable cap in a conventional manner. Electrical shielding of the indicating half cell conductor 30 would be provided by a conductive shrink tube coaxially circumscribing and secured by a shrink fit to the body of electrode 12 throughout the length thereof and electrically connected to the shielding layer 52 of cable 48. It will also be evident that while a preferred embodiment of the invention has been shown and described, various modifications may be made therein without departing from the spirit and scope of the invention as defined in the following claims.

What is claimed is:

1. An electrochemical combination pH electrode assembly comprising:
   an elongated, generally tubular, glass pH electrode body having a generally flat pH-sensitive glass membrane closing one end thereof;
   a constriction within the electrode body intermediate the ends thereof and defining a capillary passage through the constriction;
   an internal electrolyte reservoir within the electrode body between one side of the capillary passage and the glass membrane;
   a first electrolyte in liquid form within the internal electrolyte reservoir at least to the capillary passage;
   an indicating half cell disposed in the internal electrolyte reservoir and immersed in the first electrolyte therein and having a conductor portion passing out of the reservoir to provide electrical contact for the indicating half cell;
   first elastomeric plug means adjacent and sealing the side of the capillary passage remote from the internal electrolyte reservoir for preventing formation and migration of air bubbles through the internal electrolyte reservoir to the glass membrane, the first electrolyte and the first plug means defining a compressible air pocket within the capillary passage into which the first electrolyte can expand, the capillary passage being dimensioned to exhibit a sufficiently high surface tension to preclude transfer of air in the capillary passage to the internal electrolyte reservoir irrespective of the orientation of the electrode assembly whereby formation and migration of air bubbles through the internal electrolyte reservoir to the glass membrane are precluded;
   an elongated, generally tubular, plastic container coaxially surrounding the electrode body and together therewith defining an annular reference electrolyte reservoir therebetween;
   a second electrolyte in gel form within the annular reservoir;
   a reference half cell disposed in the annular reservoir and immersed in the second electrolyte therein and having a conductor portion thereof passing out of the reservoir to provide electrical contact for the reference half cell;
   a liquid junction structure surrounding the glass membrane for providing communication between a sample to be measured and the annular reservoir — the glass membrane, the liquid junction structure, and the end of the plastic container surrounding both defining a generally flat sensing portion of the electrode assembly at one end thereof;
   second elastomeric plug means situated in contact with the second electrolyte sealing the latter within the annular reservoir for preventing formation and migration of air bubbles through the annular reservoir to the liquid junction structure;
   conductor means disposed at an end of the electrolyte assembly opposite the sensing end thereof for providing electrical contact to the indicating and reference half cell conductor portions; and
   means for shielding the indicating half cell from outside electrical interference substantially throughout the length thereof, the shielding means including
   the seond electrolyte within the annular reservoir,
   a cup-shaped conductive cap, the cap having a base portion closing the opposite end of the assembly and a sidewall portion extending therefrom coaxially along the tubular plastic container and circumscribing a portion of the annular reservoir and the second electrolyte therein, the sidewall portion of the cap further providing a handle surface for holding and manipulating the electrode assembly, and
   means electrically connecting the conductive cap to the reference half cell conductor whereby the conductive cap and the second electrolyte within the annular reservoir combine to electrically shield the indicating half cell substantially throughout the length thereof.

2. The electrode assembly of claim 1 wherein the means for electrically connecting the conductive cap to the reference half cell conductor includes a conductive spring within the conductive cap, the spring being electrically connected to the reference half cell conductor portion and being biased into electrically conductive, pressure contact with the base of the conductive cap.

3. The electrode assembly of claim 2 wherein the conductor means includes a shielded coaxial cable having a conductor electrically connected to the indicating half cell conductor portion and a shielding layer surrounding and shielding the conductor and electrically connected to the conductive spring, the reference half cell conductor portion, and the conductive cap, the coaxial cable extending from the electrode assembly through the base portion of the conductive cap.

4. The electrode assembly of claim 3 wherein the liquid junction structure includes first and second loops of capillary material each having the loop portion thereof disposed in the annular reservoir contacting the second electrolyte therein and the ends thereof terminating at the flat sensing portion of the electrode assembly at spaced points surrounding the pH-sensitive glass membrane to ensure contact between the sample and at least one end of one loop of capillary material.

5. An electrochemical combination electrode assembly comprising:
an elongated, generally tubular electrode body having an ion-sensitive structure closing one end thereof;
an internal electrolyte reservoir within the electrode body adjacent the ion-sensitive structure;
a constriction within the electrode body intermediate the ends thereof and defining a capillary passage through the constriction having one side adjacent the internal electrolyte reservoir;
a first electrolyte within the internal electrolyte reservoir;
an indicating half cell disposed in the internal electrolyte reservoir and immersed in the first electrolyte therein and having a conductive portion passing out of the reservoir to provide electrical contact for the indicating half cell;
first elastomeric plug means sealing a side of the capillary passage remote from the internal electrolyte reservoir to seal the first electrolyte within the internal electrolyte reservoir for preventing formation and migration of air bubbles through the internal electrolyte reservoir to the ion-sensitive structure;
an elongated, generally tubular container coaxially surrounding the electrode body and together therewith defining an annular reference electrolyte reservoir therebetween;
a second electrolyte within the annular reservoir;
a reference half cell disposed in the annular reservoir and immersed in the second electrolyte therein and having a conductor portion thereof passing out of the reservoir to provide electrical contact for the reference half cell;
a liquid junction structure for providing communication between a sample to be measured and the annular reservoir; and
second elastomeric plug means situated in contact with the second electrolyte sealing the latter within the annular reservoir for preventing formation and migration of air bubbles through the annular reservoir to the liquid junction structure, whereby the electrode assembly can be used in any physical orientation, each respective elastomeric plug means providing an expansive seal for the respective electrolyte reservoirs thereby compensating for differing temperature coefficients of expansion of the electrode body, the tubular container, and the first and second electrolytes.

6. The electrode assembly of claim 1 wherein the first electrolyte fills the internal electrolyte reservoir to the side of the capillary passage adjacent the internal electrolyte reservoir to define a compressible air pocket within the capillary passage into which the first electrolyte can expand, the capillary passage being dimensioned to exhibit a sufficiently high surface tension to preclude the transfer of air in the capillary passage to the internal electrolyte reservoir irrespective of the orientation of the electrode assembly whereby formation and migration of air bubbles through the internal electrolyte reservoir to the ion-sensitive structure are precluded.

7. An electrochemical combination electrode assembly comprising:
an elongated, generally tubular electrode body having an ion-sensitive structure closing one end thereof;
an internal electrolyte reservoir within the electrode body adjacent the ion-sensitive structure;
a first electrolyte within the internal electrolyte reservoir;
an indicating half cell disposed in the internal electrolyte reservoir and immersed in the first electrolyte therein and having a conductive portion passing out of the reservoir to provide electrical contact for the indicating half cell;
first elastomeric plug means sealing the first electrolyte within the internal electrolyte reservoir for preventing formation and migration of air bubbles through the internal electrolyte reservoir to the ion-sensitive structure;
an elongated, generally tubular container coaxially surrounding the electrode body and together therewith defining an annular reference electrolyte reservoir therebetween;
a second electrolyte within the annular reservoir;
a reference half cell disposed in the annular reservoir and immersed in the second electrolyte therein and having a conductor portion thereof passing out of the reservoir to provide electrical contact for the reference half cell;
a liquid junction structure for providing communication between a sample to be measured and the annular reservoir;
second elastomeric plug means situated in contact with the second electrolyte sealing the latter within the annular reservoir for preventing formation and migration of air bubbles through the annular reservoir to the liquid junction structure, whereby the electrode assembly can be used in any physical orientation;
conductor means disposed at an opposite end of the electrode assembly remote from the ioon-sensitive structure for providing electrical contact to the indicating and reference half cell conductor portions, and
means for shielding the indicating half cell from outside electrical interference, the shielding means including
the second electrolyte within the annular reservoir,
a cup-shaped conductive cap at the opposite end of the electrode assembly, the cap having a base portion closing the opposite end of the assembly and a sidewall portion extending therefrom coaxially along the tubular container and circumscribing a portion of the annular reservoir and the second electrolyte therein, the sidewall portion of the cap further providing a handle surface for holding and manipulating the electrode assembly, and means electrically connecting the conductive cap to the reference half cell conductor, whereby the conductive cap and the second electrolyte within the annular reservoir combine to electrically shield the indicating half cell substantially throughout the length thereof.

8. The electrode assembly of claim 7 wherein the means for electrically connecting the conductive cap to the reference half cell conductor includes a conductive spring within the conductive cap, the spring being electrically connected to the reference half cell conductor portion and being biased into electrically conductive, pressure contact with the base portion of the conductive cap.

9. The electrode assembly of claim 8 wherein the conductor means includes a shielded coaxial cable having a conductor electrically connected to the indicating half cell conductor portion and a shielding layer surrounding and shielding the conductor and electrically connected to the conductive spring, the reference half cell conductor portion, and the conductive cap, the coaxial cable extending from the electrode assembly through the base portion of the conductive cap.

10. An electrochemical combination electrode assembly comprising:
an elongated, generally tubular electrode body having an ion-sensitive structure closing one end thereof;
an internal electrolyte reservoir within the electrode body adjacent the ion-sensitive structure;
a first electrolyte within the internal electrolyte reservoir;
an indicating half cell disposed in the internal electrolyte reservoir and immersed in the first electrolyte therein and having a conductive portion passing out of the reservoir to provide electrical contact for the indicating half cell;
first elastomeric plug means sealing the first electrolyte within the internal electrolyte reservoir for preventing formation and migration of air bubbles through the internal electrolyte reservoir to the ion-sensitive structure;
an elongated, generally tubular container coaxially surrounding the electrode body and together therewith defining an annular reference electrolyte reservoir therebetween;
a second electrolyte within the annular reservoir;
a reference half cell disposed in the annular reservoir and immersed in the second electrolyte therein and having a conductor portion thereof passing out of the reservoir to provide electrical contact for the reference half cell;
the electrode assembly having a generally flat ion-sensing surface defined by the ion-sensitive structure and an end of the tubular container surrounding the same;
a liquid junction structure for providing communication between a sample to be measured and the annular reservoir and including first and second loops of capillary material each having the loop portion thereof disposed in the annular reservoir contacting the second electrolyte therein and the ends thereof terminating at the flat sensing surface of the electrode assembly at spaced points surrounding the ion-sensitive structure to ensure contact between the sample and at least one end of one loop of capillary material; and
second elastomeric plug means situated in contact with the second electrolyte sealing the latter within the annular reservoir for preventing formation and migration of air bubbles through the annular reservoir to the liquid junction structure, whereby the electrode assembly can be used in any physical orientation.

11. An electrochemical electrode assembly comprising:
an elongated electrode body having an ion-sensitive structure closing one end thereof;
an electrolyte reservoir within the electrode body adjacent the ion-sensitive structure;
a constriction within the electrode body intermediate the ends thereof and defining a capillary passage through the constriction having one side adjacent the electrolyte reservoir;
an electrolyte filling the electrolyte reservoir to the one side of the capillary passage;
an indicating half cell disposed in the electrolyte reservoir and immersed in the electrolyte therein and having a conductive portion passing out of the reservoir to provide electrical contact for the indicating half cell; and
elastomeric plug means sealing the electrolyte within the electrolyte reservoir by sealing a side of the capillary passage remote from the electrolyte reservoir to define a compressible air pocket within the capillary passage into which the electrolyte can expand, the capillary passage being dimensioned to exhibit a sufficiently high surface tension to preclude the transfer of air in the capillary passage to the electrolyte reservoir irrespective of the orientation of the electrode assembly for preventing formation and migration of air bubbles through the electrolyte reservoir to the ion-sensitive structure, whereby the electrode can be used in any physical orientation.

* * * * *